(12) United States Patent
Banna et al.

(10) Patent No.: US 10,252,054 B2
(45) Date of Patent: *Apr. 9, 2019

(54) DISTRIBUTED PROCESSING OF ELECTROPHYSIOLOGICAL SIGNALS

(71) Applicant: Cochlear Limited, Macquarie University (AU)

(72) Inventors: Rami Banna, Sydney (AU); Andrew Botros, Sydney (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/903,521

(22) Filed: Feb. 23, 2018

(65) Prior Publication Data

US 2018/0178010 A1 Jun. 28, 2018

Related U.S. Application Data

(62) Division of application No. 13/037,453, filed on Mar. 1, 2011, now Pat. No. 9,950,162.

(51) Int. Cl.
*A61N 1/36* (2006.01)
*A61N 1/05* (2006.01)
*A61N 1/372* (2006.01)

(52) U.S. Cl.
CPC ....... *A61N 1/36036* (2017.08); *A61N 1/0541* (2013.01); *A61N 1/37217* (2013.01)

(58) Field of Classification Search
CPC .......... A61N 1/36036–1/36039; A61N 1/0541
See application file for complete search history.

(56) References Cited

U.S. PATENT DOCUMENTS 5,464,435 A 11/1995 Neumann
6,067,474 A 5/2000 Schulman et al.
(Continued)

FOREIGN PATENT DOCUMENTS

CN 101325442 A 12/2008
CN 101645858 A 2/2010
(Continued)

OTHER PUBLICATIONS

English Translation of Third Office Action in corresponding Chinese Application No. 2012800089387, dated Mar. 9, 2016, 5 pages.
(Continued)

*Primary Examiner* — George R Evanisko
(74) *Attorney, Agent, or Firm* — Edell, Shapiro & Finnan, LLC

(57) ABSTRACT

The present application discloses systems and methods for distributed processing of electrophysiological signals. The system may include a processor, a remote device, and an implant comprising an array of electrodes. The method may comprise the processor receiving an electrophysiological signal request from the remote device that specifies at least one electrode at the implant from which to receive an electrophysiological signal, transmitting to the implant instructions to apply a plurality of stimuli via the specified at least one electrode and, for individual stimuli in the plurality of stimuli, recording an electrophysiological signal component resulting from the stimulus. The method may also comprise the processor combining the recorded individual electrophysiological signal components to produce the electrophysiological signal and transmitting the electrophysiological signal to the remote device for further processing. In some embodiments of the method, the processor may compress the electrophysiological signal before transmitting it to the remote device.

20 Claims, 8 Drawing Sheets

(56) References Cited

U.S. PATENT DOCUMENTS

| | | | |
|---|---|---|---|
| 6,195,585 B1 * | 2/2001 | Karunasiri | A61N 1/36036 |
| | | | 607/57 |
| 6,205,360 B1 | 3/2001 | Carter et al. | |
| 6,415,185 B1 | 7/2002 | Martin | |
| 6,751,505 B1 | 6/2004 | Van Den Honert et al. | |
| 7,155,289 B1 | 12/2006 | Hartley | |
| 7,206,640 B1 | 4/2007 | Overstreet | |
| 7,747,329 B2 | 6/2010 | Litvak et al. | |
| 7,818,066 B1 | 10/2010 | Palmer | |
| 9,950,162 B2 * | 4/2018 | Banna | A61N 1/0541 |
| 2004/0152946 A1 | 8/2004 | Franck | |
| 2005/0107844 A1 | 5/2005 | Van Den Honert et al. | |
| 2008/0221640 A1 | 9/2008 | Overstreet et al. | |
| 2008/0319508 A1 | 12/2008 | Botros et al. | |

FOREIGN PATENT DOCUMENTS

| | | |
|---|---|---|
| CN | 101788335 A | 7/2010 |
| WO | 2009/147596 A1 | 12/2009 |

OTHER PUBLICATIONS

Examination Report in counterpart Australian Application No. 2012222959, dated Sep. 8, 2015, 3 pgs.
English translation of Office Action in counterpart Chinese Application No. 201280008938.7, dated Aug. 17, 2015, 11 pgs.
European Search Report for European Patent Application 12752729.9 dated Aug. 14, 2014.
PCT Search Report for International Application No. PCT/IB2012/000376 dated Oct. 30, 2012, 8 pgs.

* cited by examiner

DISTRIBUTED PROCESSING OF ELECTROPHYSIOLOGICAL SIGNALS

CROSS-REFERENCE TO RELATED APPLICATIONS

The present application is a divisional application of U.S. patent application Ser. No. 13/037,453, entitled "Distributed Processing of Electrophysiological Signals," filed on Mar. 1, 2011. The entire contents of which are incorporated herein by reference.

BACKGROUND

Cochlear implants may provide a person having sensorineural hearing loss with the ability to perceive sound by stimulating the person's auditory nerve via an array of electrodes implanted in the person's cochlea. An external component of the cochlear implant detects sound waves, which are converted into a series of electrical stimulation signals delivered to the implant recipient's auditory nerve via the array of electrodes. Stimulating the auditory nerve in this manner may enable the cochlear implant recipient's brain to perceive a hearing sensation that is similar to the natural hearing sensation delivered to the auditory nerve.

The effectiveness of the cochlear implant depends not only on the design of the cochlear implant itself but also on how well the cochlear implant is configured for or "fitted" to an implant recipient. The fitting of the cochlear implant, sometimes also referred to as "programming" or "mapping," creates a set of configuration settings and other data that defines the specific characteristics of the stimulation signals delivered to the implant recipient's auditory nerve. This configuration information is sometimes referred to as the recipient's "program" or "MAP."

The fitting of the cochlear implant often involves a process that may be called monitoring in which stimulation signals, or simply "stimuli", are applied via particular electrodes in the cochlear implant and responses to the stimuli are recorded. For each stimulus, a response will be generated by activity within the fibers of the auditory pathway that results from the stimulus. The response may be, for example, an evoked potential from the auditory pathway.

Individually, the responses may be referred to as "electrophysiological signal components." In order to monitor the responses, several stimuli may be applied and several electrophysiological signal components may be recorded. The electrophysiological signal components may then be combined through one or more of averaging, addition, subtraction, or other methods to produce what may be referred to as an "electrophysiological signal." Examples of an electrophysiological signal include an electrically-evoked compound action potential (ECAP), an electrically-evoked auditory brainstem response (EBAR), a cortical evoked potential (CEP), and an electrical stapedius reflex (ESR). Other examples are possible as well.

The effectiveness of the cochlear implant additionally depends on continued operation of the cochlear implant during use. For this reason, subsequent monitoring of the cochlear implant may be desirable. To this end, the cochlear implant may be designed to regularly transmit responses to a central database via, for example, a wireless network. The responses may be analyzed in order to evaluate the performance of the cochlear implant.

Thus, monitoring both during fitting and during use of the cochlear implant may aid in improving the effectiveness of the cochlear implant.

Typical systems for monitoring a cochlear implant may include an analyzing device and a recording device. The analyzing device and the recording device are typically connected by one or more physical wires (such as a communication cable), and the recording device is typically communicatively coupled to the cochlear implant by, for example, one or more physical wires or a radio link. The analyzing device may be, for example, a computer. The analyzing device may typically be designed to be capable of intense data mining and computing. The recording device may be, for example, a sound processor, such as one worn behind the recipient's ear. The recording device may typically be designed primarily as a transducer, and may not generally be capable of intense data mining and computing.

During use of the monitoring system, the analyzing device typically identifies a particular electrode or set of electrodes in the cochlear implant through which to provide stimuli in order to receive a desired electrophysiological signal. The analyzing device sends to the recording device an indication of the particular electrode(s), and the recording device transmits to the cochlear implant instructions to apply stimuli via the particular electrode(s). The recording device then records the resulting electrophysiological signal components and passes each of the recorded electrophysiological signal components back to the analyzing device for analysis and processing.

However, one drawback of typical monitoring systems is that large amounts of information must be transmitted between the analyzing device and the recording device. As an example, each electrophysiological signal component must be transmitted from the recording device to the analyzing device. In some cases, this may be as many as 35 signals, and each signal may be 32×1 6 bits. This large volume of information places stringent requirements on both the throughput and the reliability of the link between the analyzing and recording devices. While the physical wires used in typical monitoring systems to connect the recording and analyzing devices may meet these requirements, they also limit the flexibility of the monitoring system. In many applications, it may be desirable to replace the physical wire with a more flexible and convenient wireless link. However, such use of a wireless link is currently not practical because of the stringent throughput and reliability requirements.

SUMMARY

The present application discloses systems and methods for processing electrophysiological signals. In an embodiment, the method may include a processor receiving an electrophysiological signal request from a remote device that specifies at least one electrode of an implant from which to receive an electrophysiological signal. In response to the receiving the electrophysiological signal request, the processor may instruct the implant to apply a plurality of stimuli via the specified electrode(s). For individual stimuli, the processor may record an electrophysiological signal component resulting from the stimulus. The processor may also combine the individual recorded electrophysiological signal components to produce the electrophysiological signal requested by the remote device, and may transmit the electrophysiological signal to the remote device for further processing.

In an embodiment, the electrophysiological signal request may further specify a stimulation level, such as a current level. In this embodiment, the processor may further instruct the implant to apply the stimuli at the specified stimulation level.

In an embodiment, the processor may also compress the electrophysiological signal to produce a compressed electrophysiological signal, and may transmit the compressed electrophysiological signal to the remote device. Compressing the electrophysiological signal may involve, for example, source-code compression, removing a direct current (DC) offset, normalizing, truncating the electrophysiological signal, and reducing the resolution of the electrophysiological signal.

In an embodiment, the electrophysiological signal components may be evoked potentials from the auditory pathway, such as compound action potentials from the auditory nerve.

In an embodiment, the processor and the remote device may be connected via a wireless link, such as a low-bit-rate wireless link. In this embodiment, the processor may transmit the electrophysiological signal to the remote device over the wireless link.

In an embodiment, the processor may also determine whether one or more of the electrophysiological signal components is distorted. In this embodiment, the processor may instruct the implant to re-apply the plurality of stimuli via the specified electrode(s), and the processor may re-record the electrophysiological signal components. If the distortion of the one or more electrophysiological signal components is associated with amplifier saturation, the processor may use a decreased amplifier gain to avoid amplifier saturation, and/or may use a different stimulus waveform to avoid amplifier saturation.

A device for use in a system for processing electrophysiological signals is also disclosed. In an embodiment, the device may include an input configured to receive an electrophysiological signal request from a remote device that specifies at least one electrode from which to receive an electrophysiological signal. The device may also include a first output configured to transmit instructions to apply a plurality of stimuli via the specified electrode(s).

The device may also include a recording module configured to record, for individual stimuli in the plurality of stimuli, an electrophysiological signal component resulting from the stimulus, as well as a combiner configured to combine the individual recorded electrophysiological signal components to produce the electrophysiological signal. The device may also include a second output configured to transmit the electrophysiological signal to the remote device for further processing.

In an embodiment, the device may also include a compressor configured to compress the electrophysiological signal to produce a compressed electrophysiological signal. In this embodiment, the second output may be further configured to transmit the compressed electrophysiological signal.

In an embodiment, the device may also include logic configured to detect distortion of the electrophysiological signal components.

In an embodiment, one or both of the input and the second output may be a wireless interface. The first output may be a first coil. The first coil may be communicatively coupled to a second coil that is communicatively coupled to an implant. The implant may include a plurality of electrodes including the specified electrode(s).

In an embodiment, the device may be partially or entirely contained within an implant. In an embodiment, the device may be wearable by a user.

A system for processing electrophysiological signals is also disclosed. The system may include a remote device configured to create and transmit an electrophysiological signal request specifying at least one electrode. The remote device may be a handheld wireless computing device. The system may also include a processor. The processor may be, for example, the device described above. In an embodiment, the processor may be communicatively coupled to an implant. The implant may include a plurality of electrodes including the specified electrode(s).

A system for monitoring a cochlear implant is also disclosed. The system may include a cochlear implant including a plurality of electrodes in contact with a plurality of nerve stimulation sites inside a cochlea. In an embodiment, the cochlear implant may also include a transducer. The system may also include a remote device, such as the remote device described above, and a sound processor, which may be similar to the processor described above.

DETAILED DESCRIPTION

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

1. Cochlear Implant Overview

Figure 1:
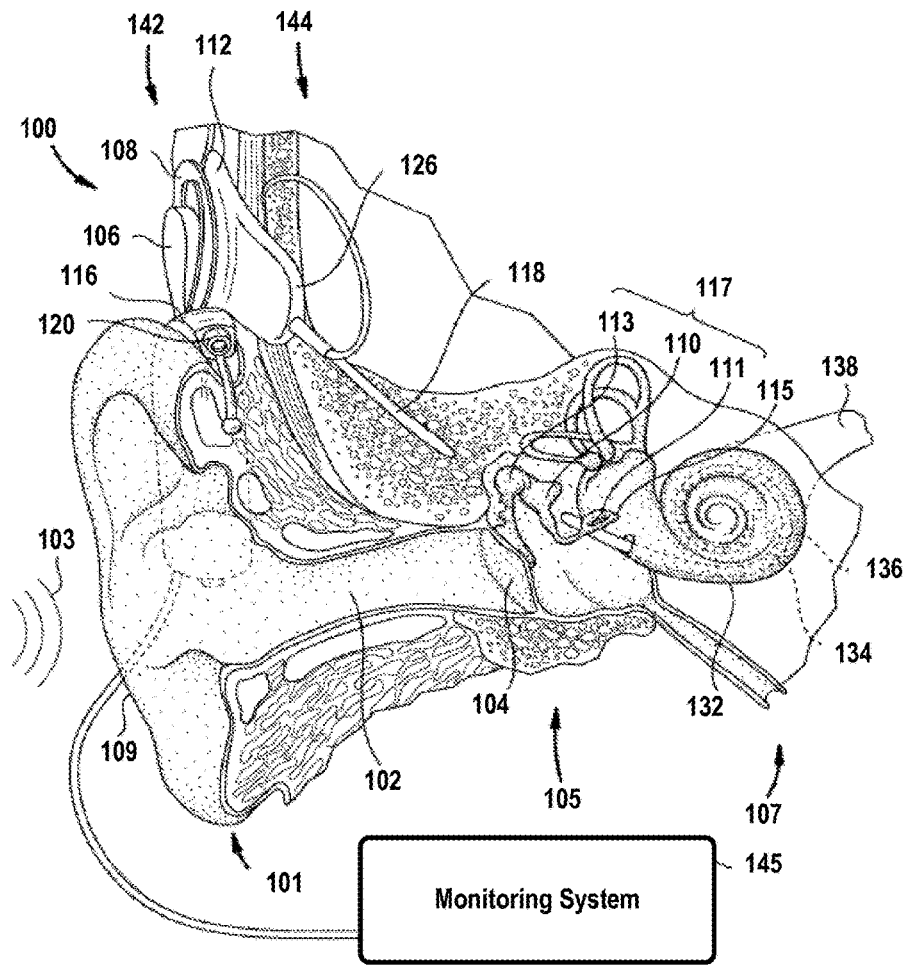
FIG. 1 shows an example of a cochlear implant that may be implanted into a cochlear implant recipient.

FIG. 1 shows an example of a cochlear implant that may be implanted into an implant recipient. The relevant components of the recipient's outer ear 101, middle ear 105, and inner ear 107 are described herein, followed by a description of the cochlear implant 100.

For persons without certain types of hearing impairments, an acoustic pressure or sound wave 103 is collected by the auricle 109 and channeled into and through the ear canal 102. The tympanic membrane 104 is located at the distal end of the ear canal 102. The tympanic membrane 104 vibrates in response to the acoustic wave 103.

The vibration of the tympanic membrane 104 is coupled to the oval window or fenestra ovalis 115 through three bones of the middle ear 105, collectively referred to as the ossicles 117, and including the malleus 113, the incus 110, and the stapes 111. For persons without particular hearing impairments, the bones 113, 110 and 111 of the middle ear 105 serve to filter and amplify the acoustic wave 103, causing the oval window 115 to articulate and/or vibrate. The vibration of the oval window 115 causes waves of fluid motion within the cochlea 132. This fluid motion within the cochlea 132, in turn, activates tiny hair cells (not shown) that line the inside of the cochlea 132. Activation of the hair cells inside the cochlea 132 causes nerve impulses to be transferred through the spiral ganglion cells (not shown) and the auditory nerve 138 to the brain (not shown), where the nerve impulses may be perceived as sound. But for persons with sensorial hearing loss, a cochlear implant may be used to create and apply electrical stimulation signals that may be detected by a person's auditory nerve and perceived as sound.

The cochlear implant 100 may include an external component assembly 142 that is directly or indirectly attached to the body of the recipient, and an internal component assembly 144 that is temporarily or permanently implanted in the recipient.

The external assembly 142 may include a sound processing unit 116 and an external transmitter unit 106. The sound processing unit 116 may include a digital signal processor (DSP), a power source to power the cochlear implant 100, and a sound transducer 120. The sound transducer 120 may be configured to detect sound and generate an audio signal, typically an analog audio signal, representative of the detected sound. In the example embodiment shown in FIG. IA, the sound transducer 120 is a microphone. In other instances, the sound transducer 120 may comprise, for example, more than one microphone, one or more telecoil induction pickup coils, or other devices now or later developed that may detect sound and generate electrical signals representative of detected sound. In some embodiments, the sound transducer 120 may not be integrated into the sound processing unit 116, but rather could be a separate component of the external component assembly 142.

The external transmitter unit 106 may include an external coil 108 of a transcutaneous energy transfer system along with the associated circuitry to drive the coil. The external transmitter unit 106 may also preferably include a magnet (not shown) secured directly or indirectly to the external coil 108.

The sound processing unit 116 may be configured to process the output of the microphone 120 that is positioned, in the depicted embodiment, near the auricle 109 of the recipient. The sound processing unit 116 may be configured to generate coded signals, referred to herein as stimulation data signals, which can be provided to the external transmitter unit 106 via a cable (not shown). The sound processing unit 116 shown in this example embodiment is designed to fit behind the auricle 109. Alternative versions may be worn on the body, or it may be possible to provide a fully implantable system which incorporates the sound processing unit into the internal component assembly 144.

The internal component assembly 144 may include an internal receiver unit 112, a stimulator unit 126 and an electrode assembly 118. The internal receiver unit 112 and the stimulator unit 126 may be hermetically sealed within a biocompatible housing.

The internal receiver unit 112 may include an internal coil (not shown) of the noted transcutaneous transfer system, along with the associated circuitry. The implanted internal receiver unit 112 may be positioned in a recess of the temporal bone adjacent to the outer ear 101 of the recipient, as shown in FIG. 1. The external coil 108 may be held in place and aligned with the implanted internal coil via the noted magnets. In one embodiment, the external coil 108 may be configured to transmit electrical signals to the internal coil via a radio frequency (RF) link.

The electrode assembly 118 may be designed to extend from the stimulator unit 126 to the cochlea 132 and to terminate in an array 134 of electrodes 136. Signals generated by the stimulator unit 126 are applied by the electrodes 136 to the cochlea 132, thereby stimulating the auditory nerve 138. While electrical stimulation of the auditory nerve 138 is typical, the electrode assembly 118 may be alternately or additionally be configured to provide mechanical stimulation to the cochlea 132, either directly by, for example, mechanically stimulating fluid within the cochlea 132, or indirectly by, for example, mechanically stimulating the middle ear.

As shown in FIG. 1, the cochlear implant 100 may be further configured to interoperate with a cochlear implant monitoring system 145. The monitoring system 145 may include, for example, a computing device, such as a personal computer, workstation, handheld computing device, or the like. As shown, the cochlear implant 100 is connected to the monitoring system 145 via a wired connection. Alternately or additionally, the cochlear implant 100 may be further configured to interoperate with one or more additional systems such as, for example, a telecommunications system. Other examples are possible as well.

2. Prior Art Monitoring Systems

Figure 2:
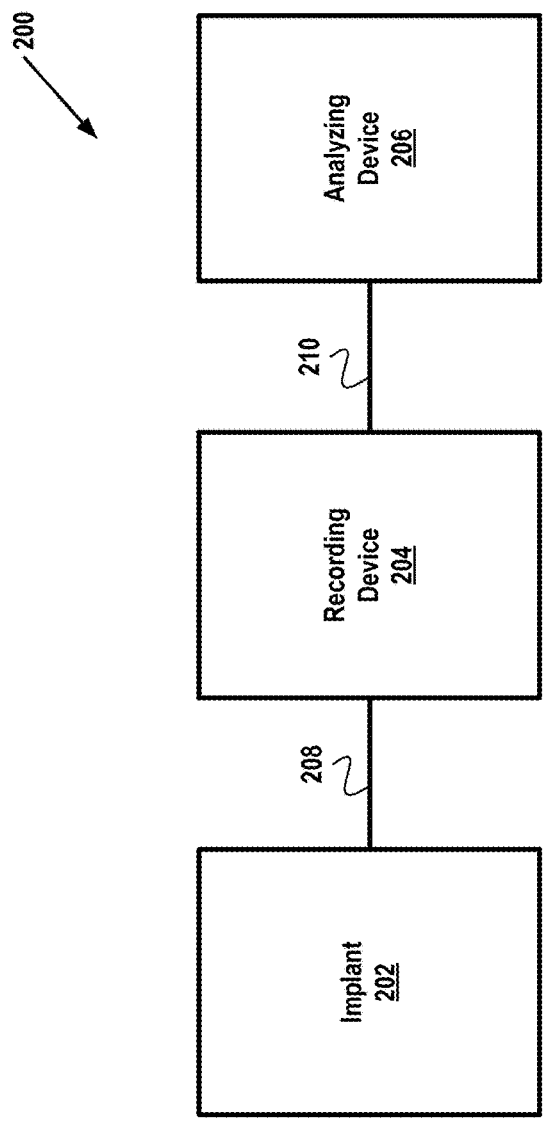
FIG. 2 shows an overview of a typical monitoring system that may be used in monitoring an implant to an implant recipient.

As noted above, a cochlear implant may be monitored both during fitting of the cochlear implant and periodically during normal use of the cochlear implant. Such monitoring may be performed by a monitoring system. FIG. 2 shows an overview of a typical monitoring system that may be used in monitoring an implant. As shown, the typical monitoring system 200 may include an implant 202, a recording device 204, and an analyzing device 206.

The implant 202 may, for example, be the cochlear implant described above in connection with FIG. 1, though similar monitoring systems may be implemented with other types of implants. The implant 202 is shown connected to the recording device 204 via a connection 208, and the recording device 204 is shown to be connected to the analyzing device 206 via a connection 210. Typically, the connection 210 may be a wired connection, such as a physical wire, because of high throughput and reliability requirements of the connection 210 in some configurations, as will be further discussed below.

A monitoring system for monitoring the implant 202 typically involves four main elements: recording, distortion detection, combining, and expert system analysis. Each of these elements will now be described.

Recording refers to the recording of the electrophysiological signal components that result from stimuli provided to an electrode or set of electrodes in the implant 202, as described above.

Distortion detection refers to the detection of electrophysiological signal components that have been distorted as a result of, for example, saturation of an amplifier in the recording device. Typically, saturation of an amplifier indicates that the stimuli provided to the implant exceeded a particular sensitivity of the implant.

Combining refers to the combining of multiple electrophysiological signal components to produce an electrophysiological signal. Combining may involve, for example, averaging the multiple electrophysiological signal components. Other examples are possible as well.

Expert system analysis refers to the automated analysis of the recorded electrophysiological signal. As an example, expert system analysis may involve monitoring the electrophysiological signal over time in order to detect any variations. As another example, expert system analysis may involve determining an ECAP threshold of each electrode in an implant. This process is sometimes referred to as Neural Response Telemetry. As yet another example, expert system analysis may involve determining one or more ECAP thresholds concurrently with one or more psychophysics measurements. As still another example, expert system analysis may involve determining one or more parameters of a neural response in order to determine an optimal operation of an implant. As yet another example, expert system analysis may involve establishing a current level profile representing a current level across one or more electrodes in an implant and adjusting one or more parameters of the current profile while a stimulation signal is applied.

Figure 3:
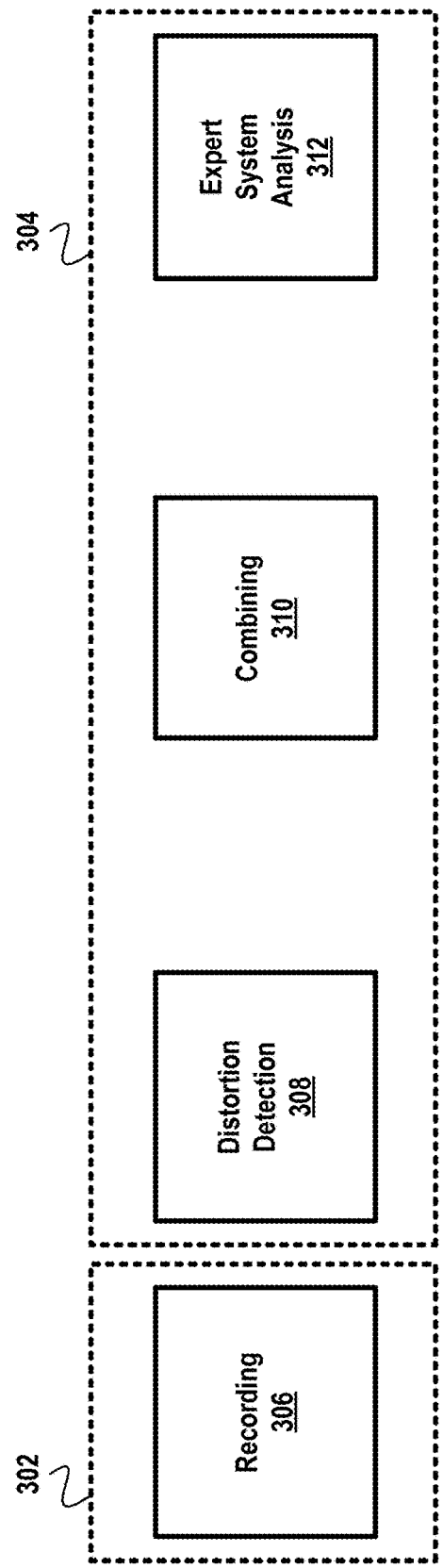
FIG. 3 shows an example distribution of monitoring system elements in a typical monitoring system.

FIG. 3 shows an example distribution of monitoring system elements in a typical monitoring system. The distribution of the elements between the recording device 302 and the analyzing device 304 is shown by the two dotted boxes.

In a typical monitoring system, the recording device 302 includes recording circuitry 306. The analyzing device 304 typically includes distortion detection circuitry 308, combining circuitry 310, and expert system analysis circuitry 312.

In particular, in a typical monitoring system, the analyzing device 304 transmits to the recording device 302 a request for an electrophysiological signal. Upon receipt of the request, the recording device 302 uses recording circuitry 306 to record the electrophysiological signal components of the requested electrophysiological signal, and transmits each of the electrophysiological signal components to the analyzing device 304 for analysis and processing including distortion detection by distortion detection circuitry 308, combining by the combining circuitry 310, and expert system analysis by the expert analysis circuitry 312. As noted above, the analyzing device 304 is typically a device designed to be capable of intense data mining and computing, such as a computer, while the recording device 302 is typically a device designed primarily as a transducer, and is generally not capable of intense data mining and computing, such as a processor.

Accordingly, the analyzing device 304 includes the majority of the computationally intensive elements (e.g., distortion detection circuitry 308, combining circuitry 310, and expert system analysis circuitry 312), whereas the recording device 302 includes only the recording circuitry 306.

As noted above, however, this distribution of the elements of the monitoring system, as is typical in prior art monitoring systems, requires the transmission of the multiple electrophysiological signal components between the recording device 302 and the analyzing device 304. This requirement translates into higher throughput and reliability requirements on the connection between the recording device 302 and the analyzing device 304.

Figure 4:
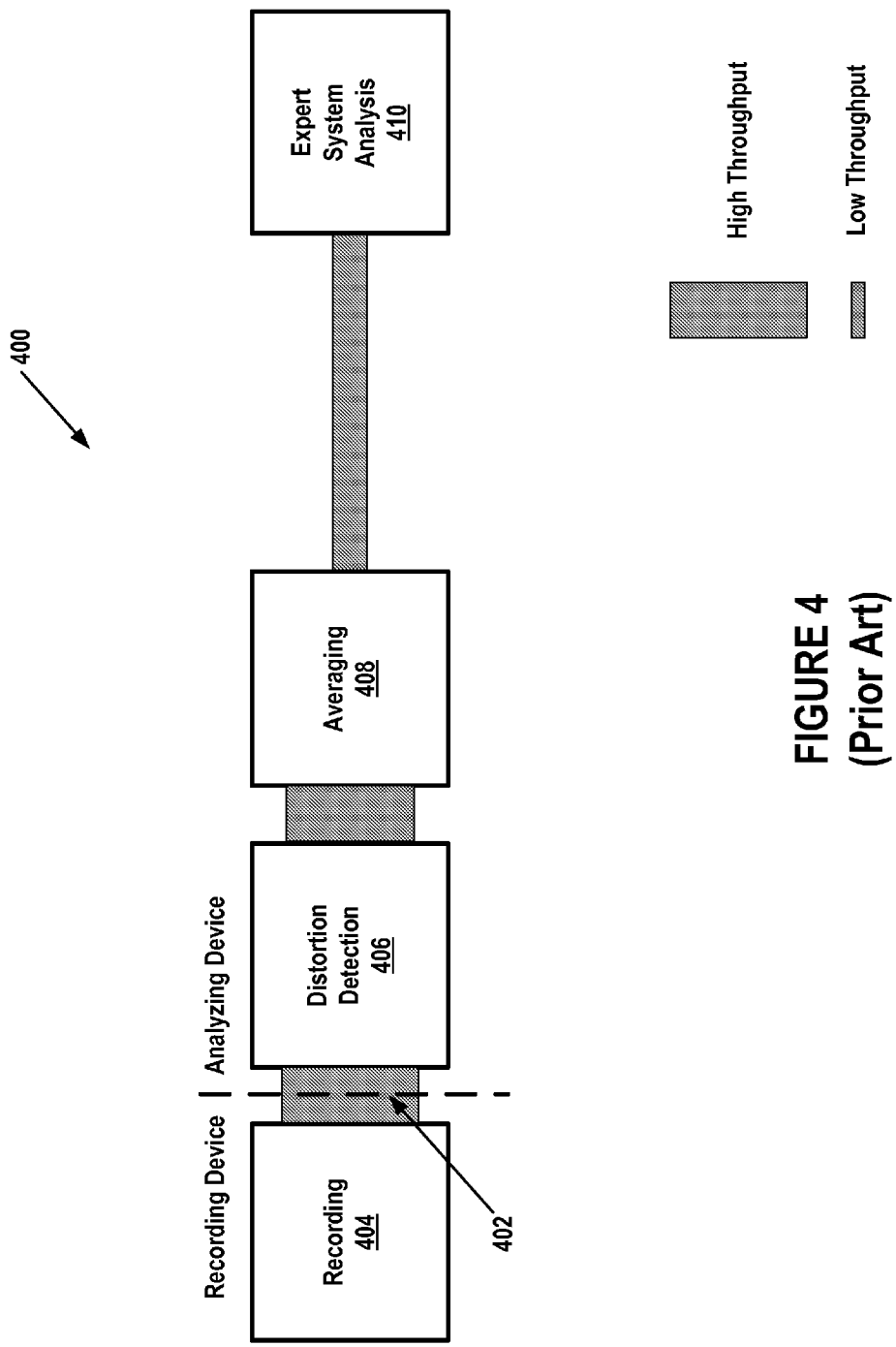
FIG. 4 shows example throughput requirements for a typical monitoring system.

FIG. 4 shows example throughput requirements for a typical monitoring system. As shown, the wider connections between the elements of the typical monitoring system 400 indicate higher throughput requirements, and the narrower connections indicate lower throughput requirements.

In the typical monitoring system 400, the largest amount of data transmission occurs between the recording circuitry 404 and analyzing device. Because, in the typical monitoring system 400, the recording circuitry 404 is included in the recording device and the remainder of the monitoring system 400 is included in the analyzing device, this means that the largest amount of data transmission in the typical monitoring system 400 occurs on the connection 402 between the recording device and the analyzing device. This large amount of data transmission on the connection 402 necessitates a high throughput requirement for the connection 402. As discussed above, such a high throughput requirement typically makes the use of a wireless connection impractical between the recording device and the analyzing device in the typical monitoring system 400.

3. System for Processing Electrophysiological Signals

It may, in many settings, be desirable to improve convenience and flexibility through the use of a wireless connection in a monitoring system. However, as shown above, the high data transmission throughput and reliability requirements of connections between recording devices and analyzing devices found in a typical monitoring system may prohibit the use of a wireless link.

Figure 5:
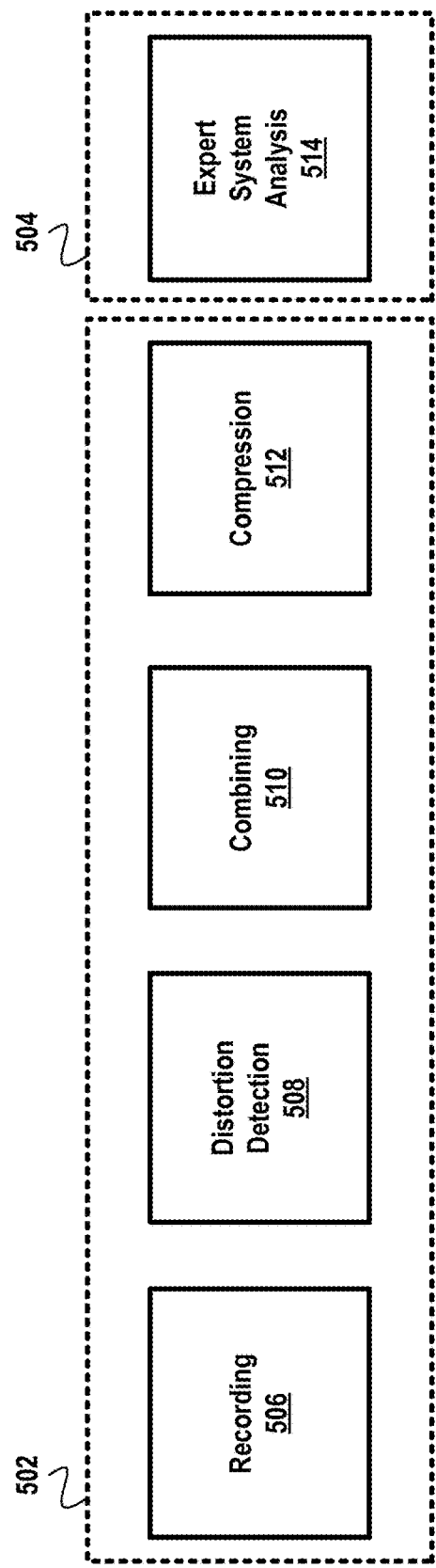
FIG. 5 shows an example distribution of monitoring system elements in an example monitoring system in accordance with an embodiment.

In the monitoring system disclosed herein, the elements of the monitoring system are redistributed among the devices in the monitoring system. An example of such redistribution is shown in FIG. 5. A comparison of FIGS. 3 and 5 may aid in illustrating the redistribution of the elements among the devices.

FIG. 5 shows an example distribution of monitoring system elements in an example monitoring system in accordance with an embodiment. For the sake of clarity, and in order to distinguish from the typical monitoring system, the devices of the example monitoring system may be referred to as a processor 502 and a remote device 504. The distribution of the elements between the processor 502 and the remote device 504 of the embodiment of FIG. 5 is shown by the two dotted boxes.

In the embodiment shown, the processor 502 includes recording circuitry 506, as does the recording device in the typical monitoring system. However, the processor 502 is shown to also include distortion detection circuitry 508, and combining circuitry 510. The remote device 504 is shown to include the expert system analysis circuitry 514.

In some embodiments, the recording circuitry 506, the distortion detection circuitry 508, and the combining circuitry 510 can be implemented on a single integrated circuit. In other embodiments, some or all of the circuitry can be implemented on separate integrated circuits, and in some embodiments, two of the recording circuitry 506, the distortion detection circuitry 508, and the combining circuitry 510 can be implemented on one integrated circuit while the remaining circuitry is implemented on one or more different integrated circuits. In some embodiments, some or all of the circuitry can be implemented as, for example, an integrated circuit with custom gate arrays or an application specific integrated circuit ("ASIC"). In some embodiments, some or all of the circuitry can be implemented with discrete hardware components. In particular, it is understood that the logic structures and method steps described herein can be implemented in dedicated hardware such as an ASIC, or as program instructions carried out by a microprocessor or other computing device.

In the example monitoring system, the processor 502 can use the recording circuitry 506 to record the electrophysiological signal components of the requested electrophysiological signal. However, instead of simply transmitting the electrophysiological signal components to the remote device 504, the processor 502 can additionally use the distortion detection circuitry 508 to determine whether any of the electrophysiological signal components is distorted, and can use the combining circuitry 510 to combine the multiple electrophysiological signal components into a single electrophysiological signal. The processor 502 can then transmit to the remote device 504 only the single electrophysiological signal (instead of the multiple electrophysiological signals). The remote device 504 can use the expert system analysis circuitry 514 to perform expert system analysis on the electrophysiological signal.

This redistribution of the elements of the monitoring system may reduce the throughput and reliability requirements of the connection between the processor 502 and the remote device 504 in at least two ways.

First, in the example monitoring system the processor 502 can transmit only the single combined electrophysiological signal (instead of the multiple electrophysiological signal components) to the remote device, which may significantly reduce the amount of information transmitted between the processor 502 and the remote device 504. This in turn may reduce the throughput and reliability requirements of the connection between the processor 502 and the remote device 504.

Second, the example monitoring system can also reduce the throughput and reliability requirements of the connection between the processor 502 and the remote device 504 by avoiding the transmission of distorted electrophysiological signal components. In the typical monitoring system, the distortion detection circuitry is included in the analyzing device (FIG. 3). Thus, the electrophysiological signal components are typically transmitted from the recording device to the analyzing device before any determination is made as to whether or not any of the electrophysiological signal components is distorted. In some cases, one or more of the transmitted electrophysiological signal components may be distorted or even unusable, such that the electrophysiological signal components must be re-requested, re-recorded, and re-transmitted before the expert system analysis may be performed. In these cases, the distorted electrophysiological signal components would be needlessly transmitted, thus needlessly increasing the amount of data transmitted between the recording device and the analyzing device.

By contrast, in the example monitoring system the distortion detection circuitry 508 can be included in the processor 502, such that the processor can use the distortion detection circuitry 508 to detect any distortion of the electrophysiological signal components before they are transmitted. In this manner, only the usable (non-distorted) electrophysiological signals are transmitted, thus reducing the amount of information transmitted between the processor 502 and the remote device 504. This in turn may reduce the throughput and reliability requirements of the connection between the processor 502 and the remote device 504. This may also reduce the amount of time required for transmission of a usable electrophysiological signal between the processor 502 and the remote device 504.

The processor 502 can additionally include compression circuitry 502, which may allow for further reduction of the throughput and reliability requirements of the connection between the processor 502 and the remote device 504. The processor 502 can use the compression circuitry 512 to compress the electrophysiological signal before transmitting it to the remote device 504, and can then transmit a compressed version of the electrophysiological signal to the remote device 504. The compression circuitry 512 can include, for example, source-code compression circuitry, circuitry configured to remove a direct current (DC) offset, circuitry configured to normalize the electrophysiological signal, circuitry configured to truncate the electrophysiological signal, and circuitry configured to reduce the resolution of the electrophysiological signal. Because the compressed electrophysiological signal may require less bandwidth for transmission than the original electrophysiological signal, including the compression circuitry 512 at the processor 502 may allow for further reduction the throughput and reliability requirements of the connection.

Thus, as a result of the redistribution of the elements of the monitoring system, the throughput and reliability requirements of the connection between the processor 502 and the remote device 504 may be lower than those of the connection between the recording device and the analyzing device of the typical monitoring system (FIG. 3). Such relaxation of the throughput and reliability requirements may allow the use of a wireless link between the processor 502 and the remote device 504, which may have not been practical between the recording device and the analyzing device.

Figure 6:
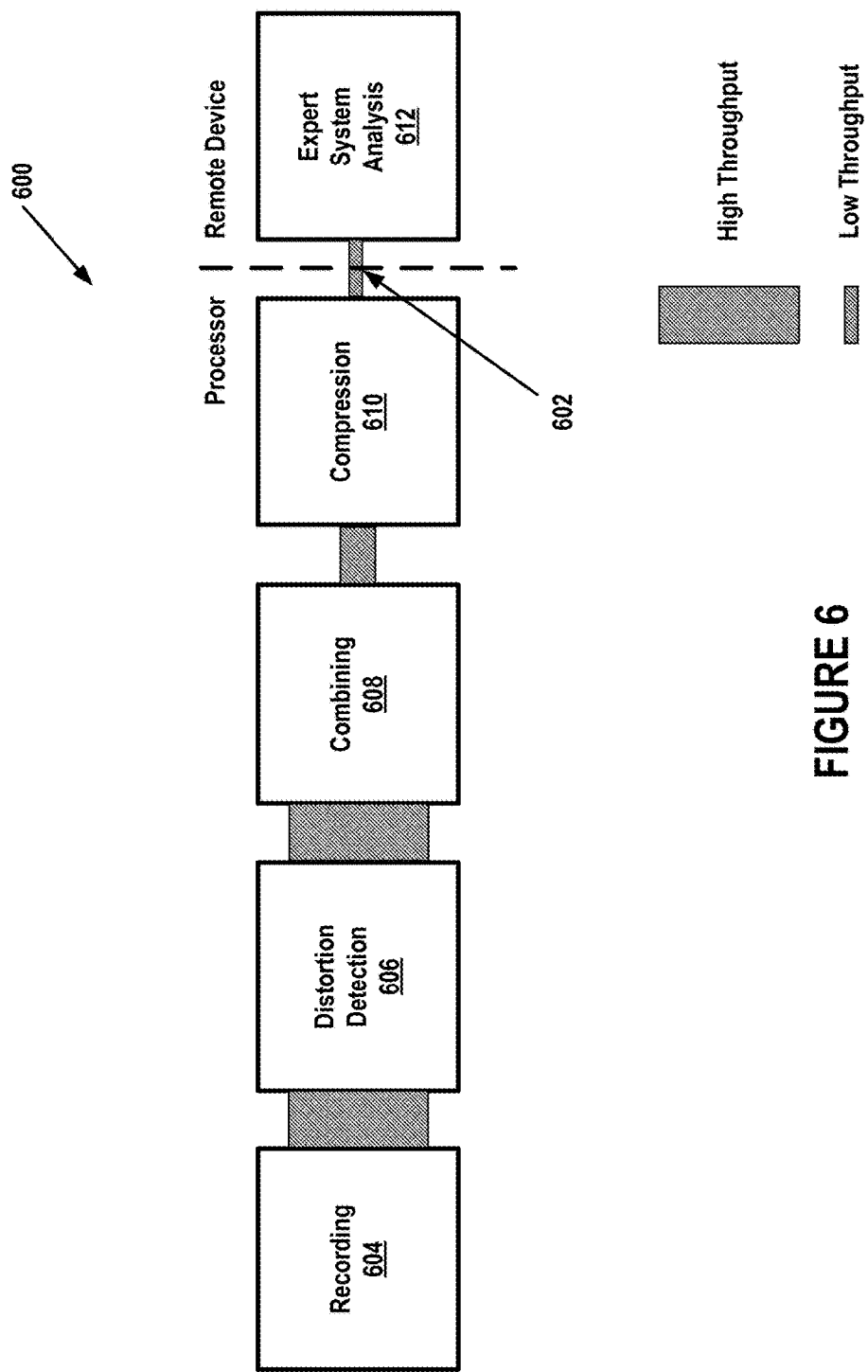
FIG. 6 shows example throughput requirements for an example monitoring system in accordance with an embodiment.

The relaxed throughput requirements of the connection between the processor 502 and the remote device 504 may be further illustrated in connection with FIG. 6. A comparison of FIGS. 4 and 6 may aid in illustrating the relaxed throughput requirements of one example monitoring system. FIG. 6 shows example throughput requirements for an example monitoring system in accordance with an embodiment.

As in FIG. 4, in FIG. 6 the wider connections between the elements of the example monitoring system 600 indicate higher throughput requirements, and the narrower connections indicate lower throughput requirements. In the example monitoring system 600, the largest amount of data transmission occurs between the recording circuitry 404 and distortion detection circuitry 406, as was the case in the typical monitoring system. However, whereas in the typical monitoring system the largest amount of data transmission occurs on the connection between the recording device and the analyzing device, in the example monitoring system 600 the recording circuitry 404 and the distortion detection circuitry 406 are both included in the processor, such that this large amount of data transmission does not occur on the connection between the processor and the remote device. Rather, as shown, in the example monitoring system 600, the connection 602 between the processor and the remote device has the lowest throughput requirement of the example monitoring system 600, which occurs between the compression circuitry 610 at the processor and the expert system analysis circuitry 612 at the remote device.

Thus, while the higher throughput requirement of the connection between the recording device and the analyzing device in the typical monitoring system may have made the use of a wireless link impractical, the lower throughput requirement of the connection 602 in the example monitoring system 600 is well-suited to the use of a wireless link for the connection 602 between the processor and the remote device. A wireless link for the connection 602 between the processor and the remote device may increase the convenience and flexibility of the example monitoring system 600 as a whole. The processor is discussed in detail in connection with FIG. 7.

Figure 7:
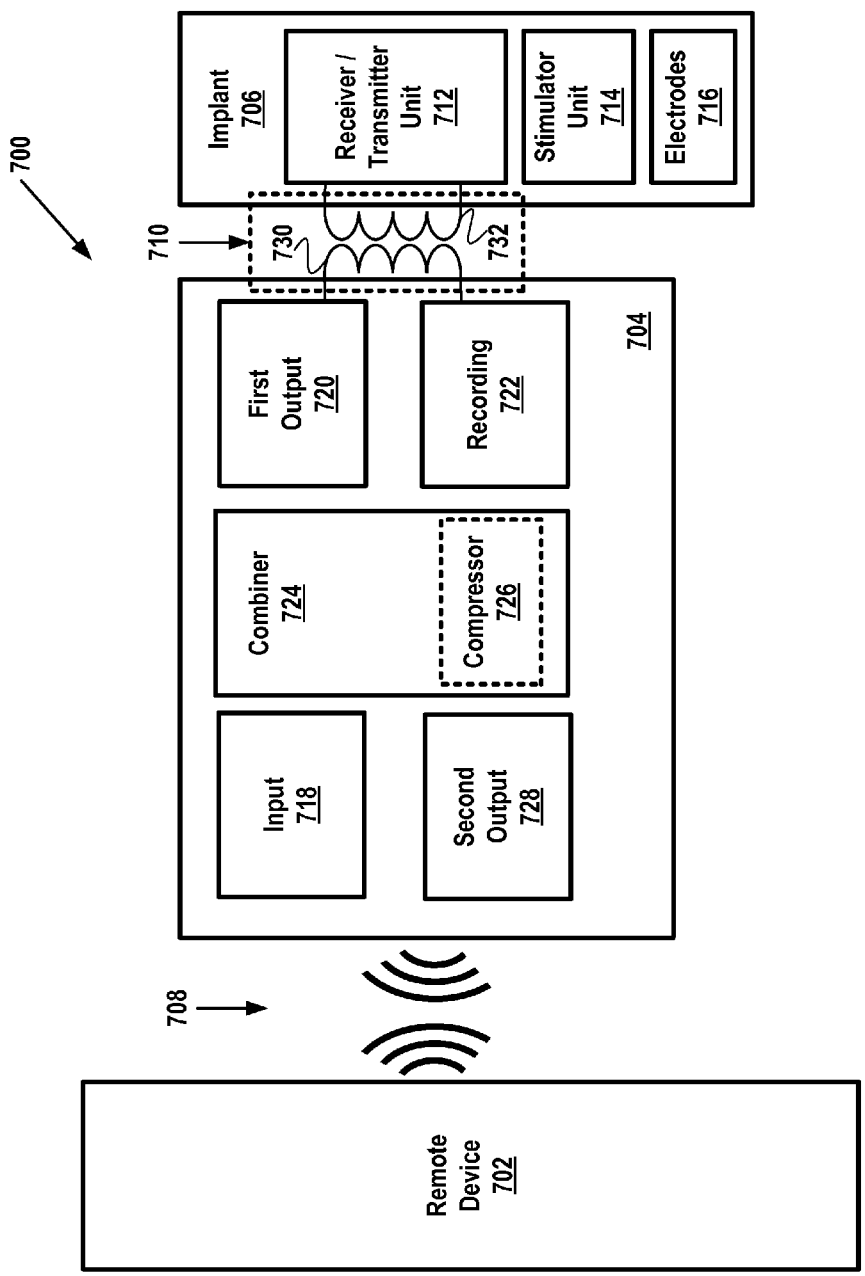
FIG. 7 shows an example monitoring system in accordance with an embodiment.

FIG. 7 shows an example monitoring system in accordance with an embodiment. As shown, the example monitoring system 700 includes a remote device 702, a processor 704, and an implant 706. The remote device 702 can be wirelessly connected to the processor 704 via wireless connection 708. Wireless connection 708 may, for example, be a low-bit-rate wireless connection. In some embodiments, the wireless connection 708 can be configured to provide reliable, secured, and/or authenticated communications between the remote device 702 and the processor 704. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms may be used as well or in addition to those listed herein to secure (and then decrypt/decode) communications.

The processor 704 can be connected to the implant 706 via communicative coupling 710.

The implant 706 can include a receiver/transmitter unit 712, a stimulator unit 714, and an array or other configuration of electrodes 716. The receiver/transmitter unit 712 can be configured to receive instructions from the processor 704 and to transmit electrophysiological signal components to the processor 704. The stimulator unit 714 can be configured to generate stimuli to be applied via the electrodes 716. In some embodiments, the stimulator unit 714 can be configured to generate stimuli according to the instructions received from the processor 704.

In some embodiments, the implant 706 can be a cochlear implant and the electrodes 716 can be in contact with a number of nerve stimulation sites inside a cochlea. In these embodiments, the implant 706 can also include a transducer. In other embodiments, the implant 706 can be another type of hearing implant, such as a direct acoustical cochlear stimulator (DACS) implant or a middle ear device.

The processor 704 can include an input 718. The input 718, connected to the wireless connection 708, can be used by the processor 704 to receive electrophysiological signal requests created and transmitted by the remote device 702. The input 718 can be, for example, a wireless interface. In some embodiments, the input 718 can include, for example, one or more wireless transceivers, such as a Bluetooth transceiver, a Wi-Fi transceiver, and/or other similar type of wireless transceiver configurable to communicate via a wireless protocol.

In an embodiment, each electrophysiological signal request may specify at least one of the electrodes 716 at the implant 706 from which to receive an electrophysiological signal. In an embodiment, each electrophysiological signal request may additionally specify a stimulation level at which to apply the stimuli via the electrodes 716. The stimulation level may be, for example, a current level.

The processor 704 can additionally include a first output 720. The first output 720, connected to communicative coupling 710, can be used by the processor 704 to send instructions to the implant 706 for applying stimuli via the electrodes 716 of the implant 706 specified in the electrophysiological signal request.

In some embodiments, the first output 720 can include a first coil 730, and the receiver/transmitter unit 712 at the implant 706 can include a second coil 732. The first coil 730 and the second coil 732 can be configured as communicative coupling 710 and can allow transmission of electrical signals between the processor 704 and the implant 706 via a radio frequency (RF) link. In these embodiments, the processor 704 may send the instructions to the implant 706 as electrical signals. The instructions may include, among other things, an indication of the electrodes 716 specified in the electrophysiological signal request. In embodiments where the electrophysiological signal request also includes a stimulation level, the instructions may also include the stimulation level.

The receiver/transmitter unit 712 at the implant 706 may receive the instructions and may pass the instructions to the stimulator unit 714. The stimulator unit 714 may then apply stimuli via the electrodes 716 specified in the electrophysiological signal request. If a stimulation level was specified, the stimulator unit 714 may apply the stimuli at the specified stimulation level. As described above, an electrophysiological signal component may result from the application of the individual stimuli.

As an example, if the implant 706 is a cochlear implant, each of the stimuli applied via electrodes 716 may cause activity within the fibers of the auditory pathway, and the activity may result in an electrophysiological signal component, such as a response in the form of an evoked electrical potential, as described above. In some embodiments, the evoked action potential may be a compound action potential from the auditory nerve.

The processor 704 can further include a recording module 722, which can include, for example, the recording circuitry described above. The recording module 722 can be used by the processor 704 to record, for individual stimuli, an electrophysiological signal component resulting from the stimulus.

The processor 704 can also include a combiner 724, which can include, for example, the combining circuitry described above. The combiner 724 can be configured to combine the recorded electrophysiological signal components to produce an electrophysiological signal. Optionally, the processor 704 can also include a compressor 726, which may include, for example, the compression circuitry described above. The compressor 726 can be configured to compress the electrophysiological signal to produce a compressed electrophysiological signal.

Lastly, the processor 704 can also include a second output 728, connected to the wireless connection 708, which can be used by the processor 704 to transmit the electrophysiological signal to the remote device 702. If the compressor 726 has been used to produce a compressed electrophysiological signal, the second output 728 can also be used by the processor 704 to transmit the compressed electrophysiological signal to the remote device 702. The second output 728 may be, for example, a wireless interface.

Thought not shown, the processor 704 can additionally include logic for detecting distortion of the electrophysiological signal components, as described above. The logic may include, for example, the distortion detection circuitry described above.

The processor 704 can additionally include one or more computer-readable storage media that can be read or accessed by the processor 704. The one or more computer-readable storage media may include volatile and/or non-volatile storage components, such as optical, magnetic, organic or other memory or disc storage. In some embodiments, the data storage may be implemented using a single physical device (e.g., one optical, magnetic, organic or other memory or disc storage unit), while in other embodiments, the data storage may be implemented using two or more physical devices.

The data storage may include computer-readable program instructions and perhaps additional data. In some embodiments, the data storage may additionally include storage required to perform at least part of the herein-described methods and/or at least part of the functionality of the herein-described systems.

While the processor 704 is shown to be distinct from the implant 706, in some embodiments, the components of the processor 704 can be partially or entirely contained within the implant 706. Alternately, in some embodiments, some components of the processor 704 can be at least partially contained within the implant 706 while other components of the processor 704 can be external to the implant 706. Alternately or additionally, the processor 704 can be wearable by a user. In some embodiments, the processor 704 can be a sound processor.

The remote device 702 can, in some embodiments, be a computing device with a wireless interface configured to communicate with the processor 704. In some embodiments, the remote device 702 can be a handheld wireless computing device. The remote device can additionally include a user interface (not shown), such as a graphical user interface, such as one or more cathode ray tubes (CRT), liquid crystal displays (LCD), light emitting diodes (LEDs), displays using digital light processing (DLP) technology, printers, light bulbs, and/or other similar devices, now know or later developed. The remote device can also include one or more user input devices (not shown), such as a keyboard, a keypad, a touch screen, a computer mouse, a trackball, a joystick, and/or other similar devices now known or later developed. The remote device can be configured to generate audible output(s) using, for example, a speaker, speaker jack, audio output port, audio output device, earphones, and/or other similar devices now known or later developed.

4. Method of Processing Electrophysiological Signals

Figure 8:
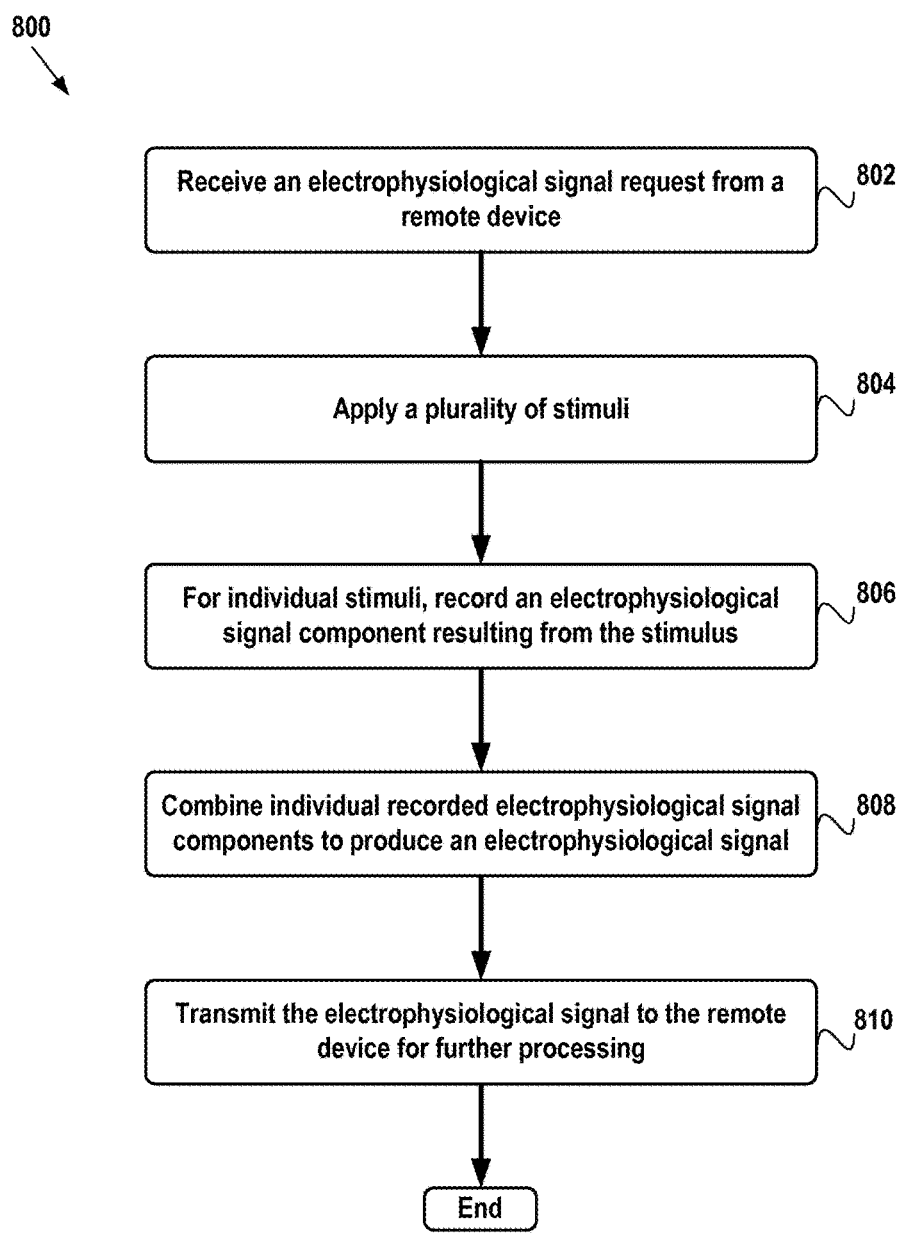
FIG. 8 shows an example method of processing electrophysiological signals.

FIG. 8 shows an example method of processing electrophysiological signals. The method 800 begins at block 802, where a processor receives an electrophysiological signal request from a remote device. The electrophysiological signal request can specify an electrode or a set of electrodes from which to receive an electrophysiological signal. In some embodiments, the electrophysiological signal request can further specify a stimulation level, such as a current level, at which to generate stimuli via the specified electrode(s).

The method 800 continues at block 804, where the processor may cause the implant to generate a plurality of stimuli via the specified electrode(s), such as by sending instructions to the implant. In embodiments where the electrophysiological signal request specified a stimulation level, the implant can generate the plurality of stimuli at the specified stimulation level.

The method 800 continues at block 806, where, for individual stimuli in the plurality of stimuli, the processor records an electrophysiological signal component resulting from the stimulus. Each of the electrophysiological signal components recorded by the processor can be evoked potentials from the auditory pathway. In particular, the component electrophysiological signals can be compound action potentials from the auditory nerve.

At block 808, the processor combines the individual recorded electrophysiological signal components to produce an electrophysiological signal. In some embodiments, the processor can additionally compress the electrophysiological signal to produce a compressed electrophysiological signal. As noted above, such compressing may involve one or more of source-code compression, removing a DC offset, normalizing, truncating the electrophysiological signal, and reducing the resolution of the electrophysiological signal.

At block 810, the processor transmits the electrophysiological signal to the remote device for further processing. In embodiments where the processor compressed the electrophysiological signal to produce a compressed electrophysiological signal, the processor can transmit the compressed electrophysiological signal to the remote device for further processing. In some embodiments, the processor can transmit the electrophysiological signal to the remote device over a wireless link, such as a low-bit-rate wireless link.

As shown, the method 800 ends after block 810. The method 800 can be repeated, or can be carried out periodically.

In some embodiments, the method 800 can further include determining whether one or more of the electrophysiological signal components is distorted. In these embodiments, if it is determined that one or more of the electrophysiological signal components is distorted, the method 800 can further include repeating blocks 804 and 806 in an effort to record non-distorted electrophysiological signal components. In particular, the method 800 can further include the processor instructing the implant to re-apply the plurality of stimuli via the specified electrode(s) and, for individual stimuli, the processor re-recording the electrophysiological signal components.

In embodiments where the distortion of the electrophysiological signal component(s) is associated with amplifier saturation, the method 800 can also include one or both of using a decreased amplifier gain and using a different stimulus waveform, both in an attempt to avoid amplifier saturation.

While the above disclosure of methods and systems for processing electrophysiological signals focused on cochlear implants and monitoring systems, the disclosure is not so limited. Many other applications exist in which electrophysiological signals are recorded and analyzed for purposes ranging from fitting and patient monitoring to therapeutic guidance. One example of such an application is pacemaker monitoring. It may be desirable to record the electrophysiological signal components of a heart that result from stimuli applied by a pacemaker. These electrophysiological signal components may be combined as described above into an electrophysiological signal, and may be transmitted wirelessly to a remote device. Other applications are possible as well.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method, comprising:
   applying a plurality of stimuli via at least one electrode;
   for individual stimuli in the plurality of stimuli, recording an electrophysiological signal component resulting from the respective stimuli to produce a plurality of recorded electrophysiological signal components;
   determining that one or more of the electrophysiological signal components is distorted;
   eliminating the one or more recorded electrophysiological signal components determined to have been distorted such that only a plurality of non-distorted recorded electrophysiological signal components remain;
   combining only the plurality of non-distorted recorded electrophysiological signal components to produce an electrophysiological signal; and
   transmitting the electrophysiological signal to the remote device.

2. The method of claim 1, further comprising:
   receiving a request for the electrophysiological signal from the remote device, wherein the request for the electrophysiological signal specifies the at least one electrode from which to receive the electrophysiological signal.

3. The method of claim 2, wherein the electrophysiological signal request further specifies a stimulation level.

4. The method of claim 3, wherein the stimulation level is a current level.

5. The method of claim 3, wherein applying the plurality of stimuli via the specified at least one electrode comprises applying the plurality of stimuli via the specified at least one electrode at the specified stimulation level.

6. The method of claim 1, further comprising:
compressing the electrophysiological signal prior to transmitting the electrophysiological signal to the remote device; and
transmitting the compressed electrophysiological signal to the remote device.

7. The method of claim 6, wherein compressing the electrophysiological signal comprises:
compressing the electrophysiological signal through one or more of source-code compression, removing a direct current (DC) offset, normalizing, truncating the electrophysiological signal, and reducing the resolution of the electrophysiological signal.

8. The method of claim 1, wherein the electrophysiological signal components comprise evoked potentials from the auditory pathway.

9. The method of claim 8, wherein the evoked potentials from the auditory pathway comprise compound action potentials from the auditory nerve.

10. The method of claim 1, wherein transmitting the electrophysiological signal to the remote device comprises:
transmitting the electrophysiological signal to the remote device over a wireless link.

11. The method of claim 10, wherein the wireless link comprises a low-bit-rate wireless link.

12. The method of claim 1, further comprising:
in response to determining that one or more of the electrophysiological signal components is distorted, re-applying stimuli that resulted in the generation of the one or more of the electrophysiological signal components determined to be distorted; and
for individual re-applied stimuli, re-recording the electrophysiological signal components to produce one or more re-recorded electrophysiological signal components.

13. The method of claim 12, further comprising:
determining that the distortion of the one or more electrophysiological signal components is associated with amplifier saturation; and
reapplying the stimuli that resulted in the generation of the one or more of the electrophysiological signal components determined to be distorted using at least one of a decreased amplifier gain to avoid amplifier saturation or a different stimulus waveform to avoid amplifier saturation.

14. A method, comprising:
applying stimulation signals via one or more electrodes implanted in a recipient;
for each of a plurality of the stimulation signals, recording an electrophysiological signal component evoked in response to the respective stimulation signal to produce a plurality of electrophysiological signal components;
determining that one or more of the plurality of electrophysiological signal components are distorted, wherein a plurality of the electrophysiological signal components are non-distorted;
combining only the plurality of electrophysiological signal components that are non-distorted to produce an electrophysiological signal; and
sending the electrophysiological signal to a remote device.

15. The method of claim 14, further comprising:
receiving a request for the electrophysiological signal from the remote device, wherein the request for the electrophysiological signal specifies the one or more electrodes from which to receive the electrophysiological signal.

16. The method of claim 15, wherein the electrophysiological signal further specifies a stimulation level.

17. The method of claim 14, further comprising:
compressing the electrophysiological signal prior to transmitting the electrophysiological signal to the remote device; and
sending the compressed electrophysiological signal to the remote device.

18. The method of claim 17, wherein compressing the electrophysiological signal request comprises:
compressing the electrophysiological signal through one or more of source-code compression, removing a direct current (DC) offset, normalizing, truncating the electrophysiological signal, and reducing the resolution of the electrophysiological signal.

19. The method of claim 14, wherein the electrophysiological signal components comprise evoked potentials from the auditory pathway.

20. The method of claim 14, wherein sending the electrophysiological signal to the remote device comprises:
sending the electrophysiological signal to the remote device over a wireless link.

* * * * *

UNITED STATES PATENT AND TRADEMARK OFFICE
CERTIFICATE OF CORRECTION

PATENT NO. : 10,252,054 B2
APPLICATION NO. : 15/903521
DATED : April 9, 2019
INVENTOR(S) : Rami Banna et al.

Page 1 of 1

It is certified that error appears in the above-identified patent and that said Letters Patent is hereby corrected as shown below:

In the Claims

Column 16, Line 29, in Claim 16, insert --request-- between signal and further;

Column 16, Line 37, in Claim 18, delete "request".

Signed and Sealed this
Twenty-fifth Day of June, 2019

Andrei Iancu
*Director of the United States Patent and Trademark Office*